United States Patent [19]

Krämer et al.

[11] Patent Number: 4,711,657
[45] Date of Patent: Dec. 8, 1987

[54] SUBSTITUTED TRIAZOLYLMETHYL TERT.-BUTYL KETONE COMPOUNDS AND PLANT PROTECTION AGENTS

[75] Inventors: Wolfgang Krämer, Wuppertal; Karl H. Büchel, Burscheid; Paul-Ernst Frohberger, Leverkusen; Wilhelm Brandes, Leichlingen; Klaus Lürssen, Bergisch Gladbach, all of Fed. Rep. of Germany

[73] Assignee: Bayer Aktiengesellschaft, Leverkusen, Fed. Rep. of Germany

[21] Appl. No.: 684,973

[22] Filed: Dec. 21, 1984

Related U.S. Application Data

[63] Continuation of Ser. No. 321,291, Nov. 13, 1981, abandoned, which is a continuation of Ser. No. 213,706, Dec. 5, 1980, abandoned.

[30] Foreign Application Priority Data

Dec. 19, 1979 [DE]  Fed. Rep. of Germany ....... 2951164

[51] Int. Cl.$^4$ .................. C07D 249/10; A61K 43/653
[52] U.S. Cl. ........................................ 71/92; 71/76; 548/262; 514/383
[58] Field of Search ................ 548/262, 101; 514/184, 514/383; 71/76, 92

[56] References Cited

U.S. PATENT DOCUMENTS

| | | | |
|---|---|---|---|
| 4,079,143 | 3/1978 | Balasubramanyan et al. | 424/269 |
| 4,243,405 | 1/1981 | Balasubramanyan et al. | 548/336 |
| 4,255,434 | 3/1981 | Krames et al. | 548/262 |
| 4,267,381 | 5/1981 | Jautelat et al. | 568/419 |

FOREIGN PATENT DOCUMENTS

| | | | |
|---|---|---|---|
| 2737489 | 2/1978 | Fed. Rep. of Germany | 424/269 |
| 1464224 | 2/1977 | United Kingdom | 548/262 |

OTHER PUBLICATIONS

Horsfall, Fungicides and Their Action, (Waltham, Mass., U.S.A., 1945), pp. 150–151.
Burger, Medicinal Chemistry, (Second Ed., New York, 1960), p. 1055.

*Primary Examiner*—Glennon H. Hollrah
*Assistant Examiner*—D. L. Dinner
*Attorney, Agent, or Firm*—Felfe & Lynch

[57] ABSTRACT

New substituted triazolylmethyl tert.-butyl ketones of the formula

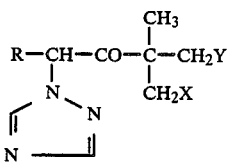

in which
R represents alkyl, alkenyl, alkynyl, optionally substituted cycloalkyl, optionally substituted cycloalkylalkyl or optionally substituted aralkyl,
X represents hydrogen or halogen and
Y represents halogen, and the acid addition salts and metal salt complexes thereof, a process for the preparation of said novel compounds, their use as plant protection agents and as intermediate products for the synthesis of other plant protection agents.

19 Claims, No Drawings

SUBSTITUTED TRIAZOLYLMETHYL TERT.-BUTYL KETONE COMPOUNDS AND PLANT PROTECTION AGENTS

This is a continuation of application Ser. No. 321,291, filed Nov. 13, 1981, which is a continuation of application Ser. No. 213,706, filed Dec. 5, 1980, both now abandoned.

This invention relates to certain new triazolylmethyl tert.-butyl ketone compounds. In additional aspect, the invention relates to plant protection agents using such compounds as active ingredients and to methods of protecting plants utilizing such compounds. In still further aspect, the invention relates to the use of such compounds as intermediates for the synthesis of other plant protection agents.

It is known that certain triazolyl ketone derivatives, for example, 1-(2,4-dichlorophenoxy)-3,3-dimethyl-1-(1,2,4-triazol-1-yl)-butan-2-one and 1-(4-chlorophenyl)-4,4-dimethyl-2-(1,2,4-triazol-1-yl)-penta-3-one have a good fungicidal activity (see DE-AS (German Published Specification) No. 2,201,063 and DE-OS (German Published Specification) No. 2,734,426). However, the action of these triazole derivatives is not always completely satisfactory in certain fields of indication, especially when small amounts and low concentrations are applied.

The present invention now provides, as new compounds, the substituted triazolylmethyl tert.-butyl ketones of the general formula

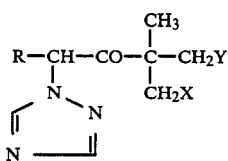

in which
R represents alkyl, alkenyl, alkynyl, optionally substituted cycloalkyl, optionally substituted cycloalkylalkyl or optionally substituted aralkyl,
X represents hydrogen or halogen and
Y represents halogen, and the acid addition salts and metal salt complexes thereof which are tolerated by plants.

The invention also provides a process for the preparation of a substituted triazolylmethyl tert.-butyl ketone of the formula (I) or an acid addition salt or metal salt complex thereof which is tolerated by plants, in which a triazolylmethyl tert.-butyl ketone of the general formula

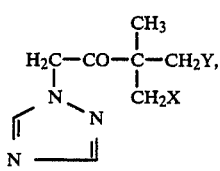

in which
X and Y have the meanings indicated above, is reacted with an alkylating agent of the general formula $$R-Z \qquad (III),$$

in which
R has the meaning indicated above and
Z represents an electron-attracting leaving group, in the presence of a base and in the presence of an organic diluent, or in an aqueous-organic two-phase system in the presence of a phase transfer catalyst, and, if required, an acid or a metal salt is then added on.

The substituted triazolylmethyl tert.-butyl ketones of the formula (I) and their salts and complexes have powerful fungicidal and plant growth-regulating properties and can therefore be used as plant protection agents.

Suprisingly, the substituted triazolylmethyl tert.-butyl ketones according to the invention exhibit a better fungicidal action than the triazolyl-ketone derivatives known from the state of the art, that is to say 1-(2,4-dichlorophenoxy)-3,3-dimethyl-1-(1,2,4-triazol-1-yl)-butan-2-one and 1-(4-chlorophenyl)-4,4-dimethyl-2-(1,2,4-triazol-1-yl)-pentan-3-one, which are closely related compounds chemically and from the point of view of their action.

The substituted triazolylmethyl tert.-butyl ketones of this invention are also interesting intermediate products for the preparation of other active compounds for the protection of plants.

The compounds according to the invention thus represent a valuable enrichment of the art.

The formula (I) provides a general definition of the substituted triazolylmethyl tert.-butyl ketones according to the invention. Preferably, in this formula,
R represents straight-chain or branched alkyl with 1 to 12 carbon atoms, straight-chain or branched alkenyl or alkynyl with in either case 2 to 12 carbon atoms, cycloalkyl which has 3 to 7 carbon atoms and is optionally substituted by alkyl with 1 to 4 carbon atoms, cycloalkylalkyl which has 3 to 7 carbon atoms in the cycloalkyl part and 1 to 4 carbon atoms in the alkyl part and is optionally substituted by alkyl with 1 to 4 carbon atoms, or optionally substituted aralkyl with 6 to 10 carbon atoms in the aryl part and 1 to 4 carbon atoms in the alkyl part, each substituent in the aryl part being selected from alkyl, alkoxy and alkylthio with in each case 1 to 4 carbon atoms, halogen, halogenoalkyl with 1 to 4 carbon atoms and 1 to 5 identical or different halogen atoms, halogenoalkoxy with 1 to 4 carbon atoms and 1 to 5 identical or different halogen atoms, halogenalkylthio with 1 to 4 carbon atoms and 1 to 5 identical or different halogen atoms, nitro, cyano, alkoxycarbonyl with 1 to 4 carbon atoms in the alkyl part, amino, alkyl- and dialkylamino with 1 to 4 carbon atoms in each alkyl part, phenylamino and phenyl and phenoxy which are optionally substituted by halogen or alkyl with 1 to 2 carbon atoms, and
X represents hydrogen and Y represents fluorine or chlorine, or
X and Y are identical and each represent fluorine or chlorine.

Particularly preferred compounds of the formula (I) are those in which R represents methyl, ethyl, n-propyl, isopropyl, n-butyl, isobutyl, sec.-butyl, tert.-butyl, vinyl, allyl, butenyl, propargyl, butynyl, cyclohexyl or cyclohexylmethyl, or benzyl or naphthylmethyl, which can optionally carry one or more substituents selected independently from methyl, ethyl, isopropyl, methoxy, methylthio, fluorine, chlorine, trifluoromethyl, trifluoromethoxy, trifluoromethylthio, nitro, cyano, phenyl and phenoxy; and X and Y have the meanings mentioned as preferred.

The following compounds of the general formula (I) may be mentioned specifically, in addition to the compounds given in the preparative examples:

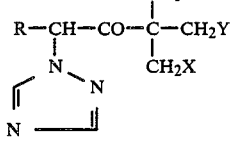
(I)

| X | Y | R |
|---|---|---|
| H | Cl | CH₃ |
| H | Cl | C₂H₅ |
| H | Cl | i-C₃H₇ |
| H | Cl | C₄H₉ |
| H | Cl | —CH₂—CH=CH₂ |
| H | Cl | —CH₂—C≡CH |
| H | Cl | cyclohexyl |
| H | Cl | —CH₂—cyclohexyl |
| H | Cl | —CH₂—C₆H₄—NO₂ |
| H | Cl | —CH₂—C₆H₄—CH₃ |
| H | Cl | —CH₂—C₆H₄—F |
| H | Cl | —CH₂—C₆H₄—Cl |
| H | Cl | —CH₂—(2-F-C₆H₄) |
| H | Cl | —CH₂—(2,4-Cl₂-C₆H₃) |
| H | Cl | —CH₂—(2-Cl-C₆H₄) |

-continued (I) formula as above

| X | Y | R |
|---|---|---|
| H | Cl | —CH₂—(3,4-Cl₂-C₆H₃) |
| H | Cl | —CH₂—C₆H₅ |
| H | Cl | —CH₂—(2,6-Cl₂-C₆H₃) |
| H | Cl | —CH₂—(2,3,4-Cl₃-C₆H₂) |
| H | F | —CH₂—cyclohexyl |
| H | F | —CH₂—CH₂—C₆H₄—Cl |
| H | F | —CH₂—(2-F-C₆H₄) |
| H | F | —CH₂—C₆H₄—CN |
| H | F | —CH₂—C₆H₄—COOCH₃ |
| Cl | Cl | CH₃ |
| Cl | Cl | C₂H₅ |
| Cl | Cl | i-C₃H₇ |
| Cl | Cl | C₄H₉ |
| Cl | Cl | —CH₂—CH=CH₂ |
| Cl | Cl | —CH₂—C≡CH |

-continued $$\underset{\underset{N}{\overset{\|}{N}}-N}{R-CH-CO-\underset{\underset{CH_2X}{\overset{CH_3}{|}}}{C}-CH_2Y} \quad (I)$$

| X | Y | R |
|---|---|---|
| Cl | Cl | cyclohexyl |
| Cl | Cl | —CH₂—cyclohexyl |
| Cl | Cl | —CH₂—C₆H₄—NO₂ |
| Cl | Cl | —CH₂—C₆H₄—CH₃ |
| Cl | Cl | —CH₂—C₆H₄—F |
| Cl | Cl | —CH₂—C₆H₄—Cl |
| Cl | Cl | —CH₂—(3,4-diCl-C₆H₃) |
| Cl | Cl | —CH₂—(2-Cl-C₆H₄) |
| Cl | Cl | —CH₂—(3-Cl-C₆H₄) |
| Cl | Cl | —CH₂—(3,4-diCl-C₆H₃) |
| Cl | Cl | —CH₂—C₆H₅ |
| Cl | Cl | —CH₂—(2,6-diCl-C₆H₃) |
| Cl | Cl | —CH₂—(3,4,5-triCl-C₆H₂) |
| F | F | CH₃ |
| F | F | C₂H₅ |
| F | F | i-C₃H₇ |
| F | F | C₄H₉ |
| F | F | —CH₂—CH=CH₂ |
| F | F | —CH₂—C≡CH |
| F | F | cyclohexyl |
| F | F | —CH₂—cyclohexyl |
| F | F | —CH₂—C₆H₄—NO₂ |
| F | F | —CH₂—C₆H₄—CH₃ |
| F | F | —CH₂—C₆H₄—F |
| F | F | —CH₂—(2-F-C₆H₄) |
| F | F | —CH₂—(2,4-diCl-C₆H₃) |

-continued $$R-CH-CO-\underset{\underset{CH_2X}{|}}{\overset{\overset{CH_3}{|}}{C}}-CH_2Y \quad (I)$$

with triazole group on CH.

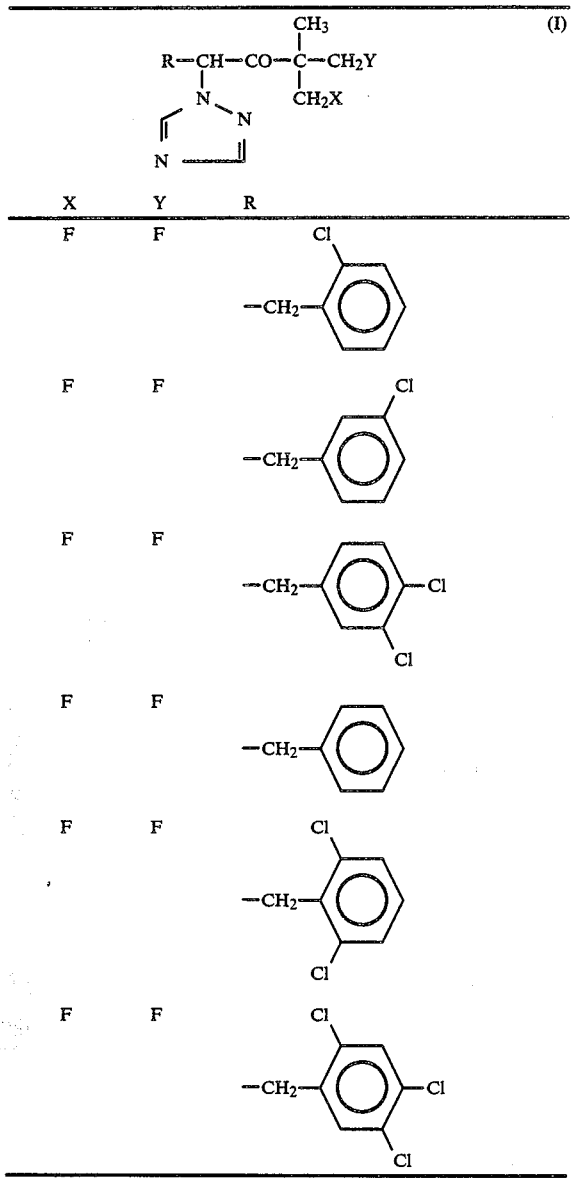

If, for example, 1-fluoro-2,2-dimethyl-4-(1,2,4-triazol-1-yl)-butan-3-one and methyl iodide are used as starting substances, the course of the reaction can be represented by the following equation:

$$H_2C-CO-\underset{\underset{CH_3}{|}}{\overset{\overset{CH_3}{|}}{C}}-CH_2F + CH_3I \longrightarrow$$

(with triazolyl on H₂C)

$$CH_3-CH-CO-\underset{\underset{CH_3}{|}}{\overset{\overset{CH_3}{|}}{C}}-CH_2F$$

(with triazolyl on CH)

The formula (II) provides a general definition of the triazolylmethyl tert.-butyl ketones required as starting substances for carrying out the process according to the invention. In this formula, X and Y preferably represent those radicals, which have already been mentioned as preferred meanings of X and Y in connection with the description of the compounds of the formula (I).

The triazolylmethyl-tert.-butyl ketones of the formula (II) are known or can be prepared according to principally known processes (see DE-OS (German Published Specification) No. 2,820,361). The compounds of the formula (II) are obtained by a process in which halogenoketones of the general formula $$Hal-CH_2-CO-\underset{\underset{CH_2X}{|}}{\overset{\overset{CH_3}{|}}{C}}-CH_2Y, \quad (IV)$$

in which
X and Y have the meanings indicated above and
Hal represents chlorine or bromine, are reacted with 1,2,4-triazole in the presence of a diluent, for example acetone, and in the presence of an acid-binding agent, for example potassium carbonate, at temperatures between 20° and 150° C.

The halogenoketones of the formula (IV) are obtained by a process in which chlorine or bromine is added to compounds of the general formula $$CH_3-CO-\underset{\underset{CH_2X}{|}}{\overset{\overset{CH_3}{|}}{C}}-CH_2Y, \quad (V)$$

in which
X and Y have the meanings indicated above, in an inert organic solvent at room temperature; or the compounds of the formula (V) are reacted, for example, with customary chlorinating agents, such as sulphuryl chloride, at 20° to 60° C. (see also the preparative examples).

Examples of the starting substances of the formula (II) which may be mentioned are: 1-chloro-2,2-dimethyl-4-(1,2,4-triazol-1-yl)-butan-3-one, 1-fluoro-2,2-dimethyl-4-(1,2,4-triazol-1-yl)-butan-3-one, 2,2-bis-chloromethyl-4-(1,2,4-triazol-1-yl)-butan-3-one and 2,2-bis-fluoromethyl-4-(1,2,4-triazol-1-yl)-butan-3-one.

The formula (III) provides a general definition of the alkylating agents also to be used as starting substances for the process according to the invention. In this formula, R preferably has those meanings which have already been mentioned as preferred for these substituents in connection with the compounds of the formula (I). Z represents an electron-attracting leaving grouping, such as preferably halogen, p-methylphenylsulphonyloxy, the grouping —O—SO₂—OR' or N⊕R₃', wherein R' preferably represents alkyl with 1 to 4 carbon atoms.

The alkylating agents of the formula (III) are generally known compounds of organic chemistry.

Possible diluents for the reaction according to the invention are inert organic solvents. These include, as preferences, aromatic hydrocarbons, such as benzene, toluene or xylene; halogenated hydrocarbons, such as methylene chloride, carbon tetrachloride, chloroform or chlorobenzene; esters, such as ethyl acetate; formamides, such as dimethylformamide; and dimethylsulphoxide.

The reaction according to the invention is carried out in the presence of a base. Any of the customary organic and, in particular, inorganic bases can be employed here, preferably alkali metal hydroxides or alkali metal carbonates, for example sodium hydroxide or potassium hydroxide.

The reaction temperatures can be varied within a substantial range in carrying out the process according to the invention. In general, the reaction is carried out between 0° and 100° C., preferably between 20° and 100° C.

In carrying out the process according to the invention, 1 to 1.2 moles of alkylating agent are preferably employed per mole of triazolylmethyl tert.-butyl ketone of the formula (II). The end products of the formula (I) are isolated in a generally customary manner.

The reaction according to the invention can also be carried out in a two-phase system, for example aqueous sodium hydroxide solution or potassium hydroxide solution/toluene or methylene chloride, if appropriate with the addition of 0.1 to 1 mol of a phase transfer catalyst, for example ammonium or phosphonium compounds, benzyl-dodecyldimethyl-ammonium chloride and triethyl-benzyl-ammonium chloride being mentioned as examples.

The compounds of the formula (I) which can be prepared according to the invention can be converted into acid addition salts or metal salt complexes.

The following acids can preferably be used for the preparation of physiologically acceptable acid addition salts of the compounds of the formula (I): hydrogen halide acids (for example hydrobromic acid and, in particular, hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) and sulphonic acids (for example p-toluenesulphonic acid and 1,5-naphthalenedisulphonic acid).

The acid addition salts of the compounds of the formula (I) can be obtained in a simple manner by customary salt formation methods, for example by dissolving a compound of the formula (I) in a suitable inert solvent and adding the acid, for example hydrogen chloride, and they can be isolated in a known manner, for example by filtration, and if appropriate purified by washing with an inert organic solvent.

Salts of metals of main groups II to IV and of subgroups I and II and IV to VIII are preferably used for the preparation of metal salt complexes of the compounds of the formula (I), examples of metals which may be mentioned being copper, zinc, manganese, magnesium, tin, iron and nickel.

Preferred anions of the salts are those which are derived from the following acids: hydrogen halide acids (for example hydrochloric acid and hydrobromic acid), phosphoric acid, nitric acid and sulphuric acid.

The metal salt complexes of the compounds of the formula (I) can be obtained in a simple manner by customary processes, thus, for example, by dissolving the metal salt in alcohol, for example ethanol, and adding the solution to the compound of the formula (I). The metal salt complexes can be purified in a known manner, for example by filtration, isolation and if appropriate by recrystallisation.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating cereal diseases, such as powdery mildew of cereal (*Erysiphe graminis*) and stripe disease of barley; Erysiphe species, such as the powdery mildew of cucumber causative organism (*Erysiphe cichoracearum*); Fusicladium species, such as the apple scab causative organism (*Fusicladium dendriticum*); and rice diseases, such as *Pellicularia sasakii* and *Pyricularia oryzae*.

The compounds according to the present invention engage in the metabolism of plants and can therefore be employed as growth regulators.

Experience to date of the mode of action of plant growth regulators has shown that an active compound can exert one or several different actions on plants. The actions of the compounds depend essentially on the point in time at which they are used, relative to the stage of development of the seed or of the plant, and on the amounts of active compound applied to the plants or their environment and the way in which the compounds are applied. In every case, growth regulators are intended positively to influence the crop plants in the desired manner.

Plant growth-regulating compounds can be employed, for example, to inhibit vegetative plant growth. Such inhibition of growth is inter alia of economic interest in the case of grasses since, by repressing the growth of grass, it is possible, for example, to reduce the frequency of cutting the grass in ornamental gardens, parks and sports grounds, at verges, at airports or in fruit orchards. The inhibition of growth of herbaceous and woody plants at verges and in the vicinity of pipelines or overland lines or, quite generally, in areas in which heavy growth is undesired, is also of importance.

The use of growth regulators to inhibit the growth in length of cereals is also important, since by shortening the stem the danger of lodging of the plants before harvesting is reduced or completely eliminated. Furthermore, growth regulators can strengthen the stem of cereals, which can counteract lodging. Use of growth regulators for shortening and strengthening the stem enables higher amounts of fertiliser to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soya or cereals. Using growth regulators it is also possible, for example, to inhibit the degradation of desired constituents, such as, for example, sugar in sugar beet or sugar cane, before or after harvesting. It is also possible favourably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that the defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree (thinning out) in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators it is furthermore possible to achieve an acceleration or retardation of ripening of the harvest product, before or after harvesting. This is of particular advantage since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators it is also possible to influence the latent period of seeds or buds of plants, so that the plants, such as, for example, pineapple or decorative plants in nurseries, germinate, shoot or blossom at a time at which they normally show no readiness to do so.

Using growth regulators it is also possible to achieve a delay in the shooting of buds or the germination of seeds, for example to avoid damage by late frosts in regions where frost is a hazard.

Finally, the resistance of plants to frost, drought or a high salt content in the soil can be induced with growth regulators. Cultivation of plants in regions which are usually unsuitable for this purpose thereby becomes possible.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

The active compounds can be converted into the customary formulations, such as solutions, emulsions, suspensions, powders, foams, pastes, granules, aerosols, very small capsules in polymeric substances and in coating compositions on seeds, as well as ULV formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations, or in the various use forms, as a mixture with other active compounds, such as fungicides, bactericides, insecticides, acaricides, nematicides, herbicides, bird repellants, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, immersion, spraying, atomising, misting, vaporising, injecting, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of in general 0.001 to 50 g, preferably 0.01 to 10 g, are employed per kilogram of seed.

For the treatment of soil, active compound concentrations of in general 0.00001 to 0.1% by weight, preferably 0.0001 to 0.02%, are employed at the place of action.

When the active compounds are used as plant growth regulators, their concentrations can be varied within a substantial range. In general, 0.01 to 50 kg, preferably 0.05 to 10 kg, of the active compounds are employed per hectare of soil surface.

The present invention also provides a fungicidal or plant-growth regulating composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention also provides a method of regulating the growth of plants which comprises applying to the plants, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

The present invention further provides plants, the growth of which has been regulated by their being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

Example 1

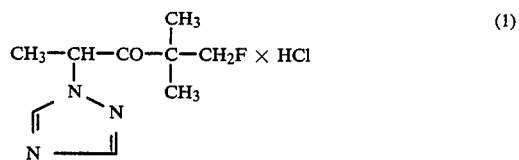

37.2 g (0.2 mol) of 1-fluoro-2,2-dimethyl-4-(1,2,4-triazol-1-yl)-butan-3-one were dissolved in 200 ml of dimethylsulphoxide, 11.2 g (0.2 mol) of potassium hydroxide, dissolved in 24 ml of water, were added and 28.4 g (0.2 mol) of methyl iodide were added dropwise at 20° C., whilst cooling. The reaction mixture was subsequently stirred at room temperature for 24 hours and poured onto 1,000 ml of water, the mixture was extracted twice with 300 ml of methylene chloride each time, the combined organic phases were washed five times with 100 ml of water each time, the organic phase was dried over sodium sulphate, the solvent was distilled off, the residue was taken up in 100 ml of acetone and the mixture was filtered and the solvent was distilled off from the mother liquor. The residue was taken up in 150 ml of ethyl acetate, and 14.4 g (0.2 mol) of hydrogen chloride were passed in. Thereafter, the product was allowed to crystallise out. 33.8 g (72% of theory) of 1-fluoro-2,2-dimethyl-4-(1,2,4-triazol-1-yl)-pentan-3-one hydrochloride of melting point 142° C. were obtained.

Preparation of the starting material:

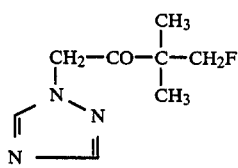

4.18 kg (35.4 mol) of 1-fluoro-2,2-dimethyl-butan-3-one were dissolved in 30 liters of methylene chloride, and 5.67 kg of bromine were added dropwise at 20° C. in the course of 2 hours such that continuous decolorisation occurred. The solvent was distilled off under a waterpump vacuum, a further 15 liters of methylene chloride were added to the residue and the solvent was again distilled off under a waterpump vacuum. The crude 1-fluoro-4-bromo-2,2-dimethyl-butan-3-one (6.97 kg, quantitative yield) was added dropwise to 2.45 kg of 1,2,4-triazole and 4.89 kg of potassium carbonate in 21.4 liters of acetone at 30° to 35° C. in the course of 2 hours, whilst cooling. The mixture was subsequently stirred at room temperature for 15 hours, the insoluble material was filtered off and the solvent was distilled off from the filtrate under a waterpump vacuum. 6.12 kg (93% of theory) of 1-fluoro-2,2-dimethyl-4-(1,2,4-triazol-1-yl)-butan-3-one, which could be further reacted directly, were obtained.

The following compounds of the general formula

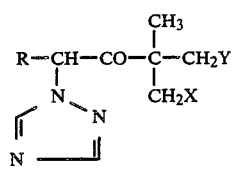

were obtained in a manner analogous to that of Example 1.

| Example No. | R | X | Y | Melting point (°C.) |
|---|---|---|---|---|
| 2 | 4-Cl-C6H4-CH2- | H | F | 78–79 |
| 3 | 2,4-Cl2-C6H3-CH2- | H | F | 112–20 |
| 4 | 2-Cl-C6H4-CH2- | H | F | 62–72 |
| 5 | 3,4-Cl2-C6H3-CH2- | H | F | 58–70 |
| 6 | C6H5-CH2- | H | F | 150 (decomp.) (×HCl) |
| 7 | 2,6-Cl2-C6H3-CH2- | H | F | 80–92 |
| 8 | 4-O2N-C6H4-CH2- | H | F | 138–40 |
| 9 | i-C3H7- | H | F | 45 (×HCl) |
| 10 | 4-H3C-C6H4-CH2- | H | F | 94 |
| 11 | C2H5 | H | F | boiling point 0.05 152 |
| 12 | C6H11- (cyclohexyl) | H | F | 128 |
| 13 | C4H9 | H | F | boiling point 0.05 163 |
| 14 | CH2=CH-CH2- | H | F | oil |
| 15 | CH≡C-CH2- | H | F | 130 (decomp.) (×HCl) |
| 16 | 4-F-C6H4-CH2- | H | F | 182 (decomp.) (×HCl) |
| 17 | 2-Cl-C6H4-CH2- | H | F | 99 |
| 18 | 2-Cl-C6H4-CH2- | H | Cl | 102 |
| 19 | 4-Cl-C6H4-CH2- | F | F | 108 |
| 20 | 2-F-C6H4-CH2- | Cl | Cl | oil |
| 21 | C6H5-CH2-CH2- | H | F | oil |
| 22 | C6H5-CH2- | F | F | oil |
| 23 | 2,4-Cl2-C6H3-CH2- | F | F | 63–78 |
| 24 | 2,4-Cl2-C6H3-CH2- | F | F | 96–112 (×HCl) (decomp.) |

-continued

| Example No. | R | X | Y | Melting point (°C.) |
|---|---|---|---|---|
| 25 | 2-Cl-C6H4-CH2- | H | Cl | 116-27 (×HCl) |
| 26 | cyclopropyl-CH2- | H | F | 107 (×HCl) (decomp.) |
| 27 | 4-F-C6H4-CH2- | H | Cl | 58-78 |
| 28 | cyclohexyl-CH2- | H | F | 88-98 (×HCl) |
| 29 | 4-Cl-C6H4-CH2- | H | Cl | 58-74 |
| 30 | CH2=CH-CH2-CH2- | H | F | oil |
| 31 | 4-Br-C6H4-CH2- | H | F | 78 |
| 32 | 4-Br-C6H4-CH2- | H | Cl | 56 |
| 33 | 4-F3C-C6H4-CH2- | H | F | 82 |
| 34 | 2-CF3-C6H4-CH2- | H | F | 86 |
| 35 | 3-CF3-C6H4-CH2- | H | F | 88 |
| 36 | 4-F3CO-C6H4-CH2- | H | F | 86-88 |
| 37 | 4-F3C-S-C6H4-CH2- | H | F | 86-92 |
| 38 | 2-F-C6H4-CH2- | H | F | 46-48 |
| 39 | 4-Cl-3-CF3-C6H3-CH2- | H | F | 53-63 |
| 40 | 2-CH3-C6H4-CH2- | H | F | 62-4 |
| 41 | C6H5-CH2- | Cl | Cl | oil $n_D^{20}$ 1,5408 |
| 42 | 3-OCH3-C6H4-CH2- | H | F | 78-81 |
| 43 | 4-NC-C6H4-CH2- | H | F | 138-41 |
| 44 | cyclohexyl-CH2- | F | F | oil $n_D^{20}$ 1,4832 |

USE EXAMPLES

The fungicidal and growth regulating activity of the compounds of this invention is illustrated by the following biotest Examples.

In these Examples, the compounds according to the present invention are each identified by the number (given in brackets) of the corresponding preparative Example.

The known comparison compounds are identified as follows:

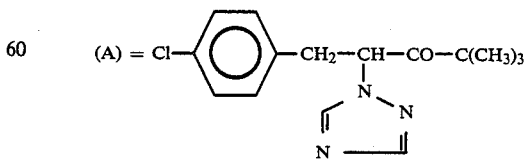

(A) = 4-Cl-C6H4-CH2-CH(triazolyl)-CO-C(CH3)3

-continued

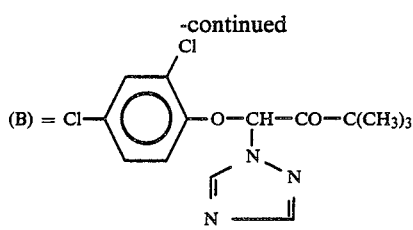

EXAMPLE A

Shoot Treatment Test/Powdery Mildew of Cereals (Leaf-Destructive Mycosis)/Protective To produce a suitable preparation of active compound, 0.25 part by weight of active compound was taken up in 25 parts by weight of dimethylformamide and 0.06 part by weight of alkylaryl polyglycol ether; 975 parts by weight of water were then added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis* var. *hordei*.

After 6 days' dwell time of the plants at a temperature of 21-22 deg. C. and 80-90% atmospheric humidity the occurrence of mildew pustules on the plants was evaluated. The degree of infection was expressed as a percentage of the infection of the untreated control plants. 0% denoted no infection and 100% denoted the same degree of infection as in the case of the untreated contol. The active compound was the more active, the lower was the degree of mildew infection.

The active compounds, active compound concentrations in the spray liquor and degrees of infection can be seen from the table which follows:

TABLE A

| | Shoot treatment test/powdery mildew of cereal/protective | |
|---|---|---|
| Active compounds | Active compound concentration in the spray liquor in % by weight | Infection in % of the untreated control |
| (A) | 0.001 | 72.5 |
| (3) | 0.001 | 0.0 |
| (5) | 0.001 | 0.0 |

EXAMPLE B

Fusicladium Test (Apple)/Protective

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated amount of emulsifier.

Young apple seedlings in the 4-6 leaf stage were sprayed with the spray liquid until dripping wet. The plants remained in a greenhouse for 24 hours at 20 degrees C and at a relative atmospheric humidity of 70%. They were then inoculated with an aqueous conidium suspension of the apple scab causative organism (*Fusicladium dendriticum*) and incubated for 18 hours in a humidity chamber at 18-20 degrees C. and at a relative atmospheric humidity of 100%.

The plants were then brought into a greenhouse again for 14 days.

15 days after inoculation, the infection of the seedlings was determined. The assessment data were converted to percent infection. 0% meant no infection; 100% meant that the plants were totally infected.

The active compounds, the concentrations of the active compounds and the results can be seen from the following table:

TABLE B

| Fusicladium test (apple)/protective | |
|---|---|
| Active compound | Infection in % at an active compound concentration of 0.00025% |
| (B) | 46 |
| (2) | 39 |

EXAMPLE C

Influence on Growth of Sugar-Beet

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Sugar beet was grown in a greenhouse until formation of the cotyledons was complete. In this stage, the plants were sprayed with the preparation of active compound until dripping wet. After 14 days, the additional growth of plants was measured and the influence on growth in percent of the additional growth of the control plants was calculated. 0% influence on growth denoted a growth which corresponded to that of the control plants. Negative values characterised an inhibition of growth in comparison to the control plants, whilst positive values characterised a promotion of growth in comparison to the control plants.

The test results are shown in the following table.

TABLE C

| Influence on growth of sugar-beet | | |
|---|---|---|
| Active compound | Concentration in % | Influence on growth in % |
| (2) | 0.05 | −45(*) (**) |
| (7) | 0.05 | −50(**) |
| Control | — | = 0 |

(*) dark green leaves
(**) thick leaves

EXAMPLE D

Inhibition of Growth of Soya Beans

Solvent: 30 parts by weight of dimethylformamide
Emulsifier: 1 part by weight of polyoxyethylene sorbitan monoclaurate To produce a suitable preparation of active compound, 1 part by weight of active compound was mixed with the stated amounts of solvent and emulsifier and the mixture was made up to the desired concentration with water.

Soya bean plants were grown in a greenhouse until the first secondary leaf had unfolded completely. In this stage, the plants were sprayed with the preparations of active compound until dripping wet. After 3 weeks, the additional growth was measured on all the plants and the inhibition of growth in percent of the additional growth of the control plants was calculated. 100% inhibition of growth meant that growth had stopped and 0% denoted a growth corresponding to that of the control plants.

The test results are shown in the following table.

TABLE D

| | Inhibition of growth of scya beans | |
|---|---|---|
| Active compounds | Active compound concentration in % | Inhibition of growth in % |
| (2) | 0.05 | 70(*) |
| Control | — | = 0 |

(*) dark green leaf coloration

EXAMPLE E

Inhibition of Growth of Cotton

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amount of solvent and emulsifier and the mixture was made up to the desired concentration with water.

Cotton plants were grown in a greenhouse until the 5th secondary leaf had unfolded completely. In this stage, the plants were sprayed with the preparations of active compound until dripping wet. After 3 weeks, the additional growth of the plants was measured and the inhibition of growth in percent of the additional growth of the control plants was calculated. 100% inhibition of growth meant that growth had stopped and 0% denoted a growth corresponding to that of the control plants.

The test results are shown in the following table.

TABLE E

| | Inhibition of growth of cotton | |
|---|---|---|
| Active compound | Concentration in % | Inhibition of growth in % |
| (2) | 0.05 | 50 |
| Control | — | = 0 |

As already mentioned, the substituted triazolylmethyl tert.-butyl ketones of the formula (I) are also interesting as intermediate products. For example, they can easily be converted into triazolylmethyl-tert.-butyl-carbinols of the general formula $$R-CH(OH)-CH(N\underset{N=N}{\overset{N}{\diagup}})-C(CH_3)(CH_2X)-CH_2Y, \quad (VI)$$

in which
R, X and Y have the meanings indicated above, by a process in which the compounds of the formula (I) are reduced by known methods, for example by reaction with a complex hydride, such as sodium borohydride, if appropriate in the presence of a polar organic solvent, for example an alcohol, at temperatures between 0° and 30° C.

The compounds of the formula (VI), which are the subject of German Patent Application No. P2951163.5 of 19th Dec., 1979 have the powerful fungicidal and plant growth regulating properties and can therefore be used as plant protection agents.

The following comparison experiment shows, for example, the superior action of 5-(4-chlorophenyl)-2,2-dimethyl-1-fluoro-4-(1,2,4-triazol-1-yl)-pentan-3-ol compared with that of the known compound (A).

EXAMPLE F

Shoot Treatment Test/Powdery Mildew of Cereals (Leaf-Destructive Mycosis)/Protective To produce a suitable preparation of active compound, 0.25 part by weight of active compound was taken up in 25 parts by weight of dimethylformamide and 0.06 part by weight of alkylaryl polyglycol ether; 975 parts by weight of water were then added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis* var. *hordei*.

After 6 days' dwell time of the plants at a temperature of 21–22 deg. C. and 80–90% atmospheric humidity the occurrence of mildew pustules on the plants was evaluated. The degree of infection was expressed as a percentage of the invention of the untreated control plants. 0% denoted no infection and 100% denoted the same degree of infection as in the case of the untreated control. The active compound was the more active, the lower was the degree of mildew infection.

The active compounds, active compound concentrations in the spray liquor and degrees of infection can be seen from the table which follows:

TABLE F

| Shoot treatment test/powdery mildew of cereal/protective | | |
|---|---|---|
| Active compounds | Active compound concentration in the spray liquor in control % by weight | Infection in % of the untreated |
| (A) | 0.001 | 72.5 |

TABLE F-continued

Shoot treatment test/powdery mildew of cereal/protective

| Active compounds | Active compound concentration in the spray liquor in control % by weight | Infection in % of the untreated |
|---|---|---|
| 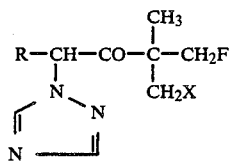 | 0.001 | 0.0 |

It will be understood that the specification and examples are illustrative, but not limitative of the present invention and that other embodiments within the spirit and scope of the invention will suggest themselves to those skilled in the art.

What is claimed is:

1. A substituted triazolylmethyl tert.-butyl ketone compound of the formula $$R-CH(N\text{-triazolyl})-CO-C(CH_3)(CH_2F)-CH_2X$$

wherein
R is cyclohexylmethyl, 4-chlorobenzyl, 2,4-dichlorobenzyl or 3,4-dichlorobenzyl, and
X is hydrogen or fluorine;

and the hydrochloric acid addition salts thereof.

2. Substituted triazolylmethyl tert.-butyl ketone compound as claimed in claim 1 designated 1-fluoro-2,2-dimethyl-4-(1,2,4-triazol-1-yl)-5-(4-chlorophenyl)-pentan-3-one.

3. Substituted triazolylmethyl tert.-butyl ketone compound as claimed in claim 1 designated 1-fluoro-2,2-dimethyl-4-(1,2,4-triazol-1-yl)-5-(2,4-dichlorophenyl)-pentan-3-one.

4. Substituted triazolylmethyl tert.-butyl ketone compound as claimed in claim 1 designated 1-fluoro-2-methyl-2-fluoromethyl-4-(1,2,4-triazol-1-yl)-5-(2,4-dichlorophenyl)-pentan-3-one.

5. Plant fungicide composition comprising, as an active ingredient, an effective amount of a substituted triazolylmethyl tert.-butyl ketone compound as claimed in claim 1, and an agriculturally acceptable carrier.

6. Plant fungicide composition as claimed in claim 5 containing from 0.0001 to 1% of the active compound by weight.

7. Plant fungicide composition as claimed in claim 5 containing from 0.001 to 0.5% of the active compound by weight.

8. Method of protecting plants from fungus growth, which method comprises applying to the plants or their habitat an effective amount of a substituted triazolylmethyl tert.-butyl ketone compound as claimed in claim 1.

9. Method as claimed in claim 8 wherein the active compound is applied to soil in an amount of 0.00001 to 0.1% by weight.

10. Method as claimed in claim 8 wherein the active compound is applied to soil in an amount of 0.0001 to 0.02% by weight.

11. Method as claimed in claim 8 wherein said active compound is applied to seed in an amount of 0.001 to 50 grams per kilogram of seed.

12. Method as claimed in claim 8 wherein said active compound is applied to seed in an amount of 0.01 to 10 gram per kilogram of seed.

13. Method as claimed in claim 8 wherein the active compound is applied to an area of agriculture in an amount of 0.01 to 50 kg per hectare.

14. Method as claimed in claim 8 wherein the active compound is applied to an area of agriculture in an amountof 0.05 to 10 kg per hectare.

15. Plant growth regulating composition comprising, as an active ingredient, an effective amount of a substituted triazolylmethyl tert.-butyl ketone compound as claimed in claim 1, and an agriculturally acceptable carrier.

16. Method of regulating plant growth comprising the steps of applying to the plants or their habitat an effective amount of a substituted triazolylmethyl tert.-butyl ketone compound as claimed in claim 1.

17. Substituted triazolylmethyl tert.-butyl ketone compound as designated 1-fluoro-2,2-dimethyl-4-(1,2,4-triazol-1-yl)-5-cyclohexylmethylpentan-3-one hydrochloride.

18. Substituted triazolylmethyl tert.-butyl ketone compound designated 1-fluoro-2-methyl-2-fluoromethyl-4-(1,2,4-triazol-1-yl)-5-cyclohexylmethylpentan-3-one.

19. Method as claimed in claim 8 where said substituted triazolylmethyl tert.-butyl ketone compound is selected from the group consisting of 1-fluoro-2,2-dimethyl-4-(1,2,4-triazol-1-yl)-5-(4-chlorophenyl)-pentan-3-one, 1-fluoro-2,2-dimethyl-4-(1,2,4-triazol-1-yl)-5-(2,4-dichlorophenyl)-pentan-3-one, 1-fluoro-2-methyl-2-fluoromethyl-4-(1,2,4-triazole-1-yl)-5-(2,4-dichlorophenyl)-pentan-3-one, 1-fluoro-2-methyl-2-fluoromethyl-4-(1,2,4-triazole-1-yl)-5-(3,4-dichlorophenyl)-pentan-3-one, 1-fluoro-2,2-dimethyl-4-(1,2,4-triazol-1-yl)-5-cyclohexylmethylpentan-3-one hydrochloride and h1-fluoro-2-methyl-2-fluoromethyl-4-(1,2,4-triazol-1-yl)-5-cyclohexylmethylpentan-3-one.

* * * * *

UNITED STATES PATENT AND TRADEMARK OFFICE
CERTIFICATE OF CORRECTION

PATENT NO. : 4,711,657

DATED : December 8, 1987

INVENTOR(S) : Wolfgang Kramer, et al.

It is certified that error appears in the above-identified patent and that said Letters Patent is hereby corrected as shown below:

Col. 24, lines 62-63, "hl-fluoro," should read --1-fluoro--.

Signed and Sealed this

Eighteenth Day of October, 1988

Attest:

DONALD J. QUIGG

Attesting Officer

Commissioner of Patents and Trademarks